United States Patent
Nomine

(10) Patent No.: US 7,334,346 B2
(45) Date of Patent: Feb. 26, 2008

(54) DEVICE AND METHOD FOR CONTROLLING DEHYDRATION DURING FREEZE-DRYING

(75) Inventor: Cyrille Nomine, Annecy (FR)

(73) Assignee: Alcatel, Paris (FR)

( * ) Notice: Subject to any disclaimer, the term of this patent is extended or adjusted under 35 U.S.C. 154(b) by 0 days.

(21) Appl. No.: 11/313,923

(22) Filed: Dec. 22, 2005

(65) Prior Publication Data

US 2006/0137212 A1 Jun. 29, 2006

(30) Foreign Application Priority Data

Dec. 23, 2004 (FR) .................................. 04 53161

(51) Int. Cl.
*F26B 13/30* (2006.01)
(52) U.S. Cl. ............................................ 34/284; 34/92
(58) Field of Classification Search ................. 34/284, 34/92; 356/316; 156/345.2
See application file for complete search history.

(56) References Cited

U.S. PATENT DOCUMENTS

| | | | |
|---|---|---|---|
| 3,020,645 A | 2/1962 | Copson | |
| 6,060,019 A | 5/2000 | Spencer | |
| 6,643,014 B2 * | 11/2003 | Chevalier et al. | 356/316 |
| 6,649,019 B2 * | 11/2003 | Bernard et al. | 156/345.29 |
| 2002/0153102 A1 * | 10/2002 | Bernard et al. | 156/345.29 |
| 2003/0116027 A1 | 6/2003 | Brulls | |
| 2004/0120869 A1 | 6/2004 | Ko | |

FOREIGN PATENT DOCUMENTS

SU 1 272 067 A1 11/1986
SU 2 272 067 A 11/1986

OTHER PUBLICATIONS

Database WPI, Section CH, Week 198728, Derwent Publications, Ltd. London, GB; AN 1987-197334, XP002337477 corresponding to SU 1 272 067 A (Med Biol Prep Stand) dated Nov. 23, 1986.
Connelly et al, "Monitor lyophillization with mass spectrometer gas analysis", Journal of Parenteral Science and Technology, vol. 47, No. 2, Mar. 1993, pp. 70-75, XP00805023.
Database WPI, Section CH, Week 198728, Derwent Publications, Ltd. London, GB; Class J08, AN 1987-197334, XP002337477 corresponding to SU 1 272 067 A (Med Biol Prep Stand) dated Nov. 23, 1986.
Connelly et al, "Monitor lyophilization with mass spectrometer gas analysis", Journal Of Parenteral Science And Technology, vol. 47, No. 2, Mar. 1993, pp. 70-75, XP00805023.

* cited by examiner

Primary Examiner—S. Gravini
(74) Attorney, Agent, or Firm—Sughrue Mion, PLLC

(57) ABSTRACT

A device for controlling dehydration during freeze-drying in an enclosure connected to a vacuum line includes an analyzer for analyzing the gases contained in the enclosure, the gas analyzer comprising a system for ionizing the gases comprising a plasma source in contact with the gases combined with a generator adapted to generate a plasma from the gases and a system for analyzing ionized gases comprising a radiation sensor situated in the vicinity of the area of generation of the plasma connected to apparatus for analyzing evolution of the radiation spectrum emitted by the plasma. The plasma source is preferably produced by inductive coupling and the analyzer for analyzing the evolution of the radiation spectrum is preferably an optical emission spectrometer.

20 Claims, 2 Drawing Sheets

FIG_1
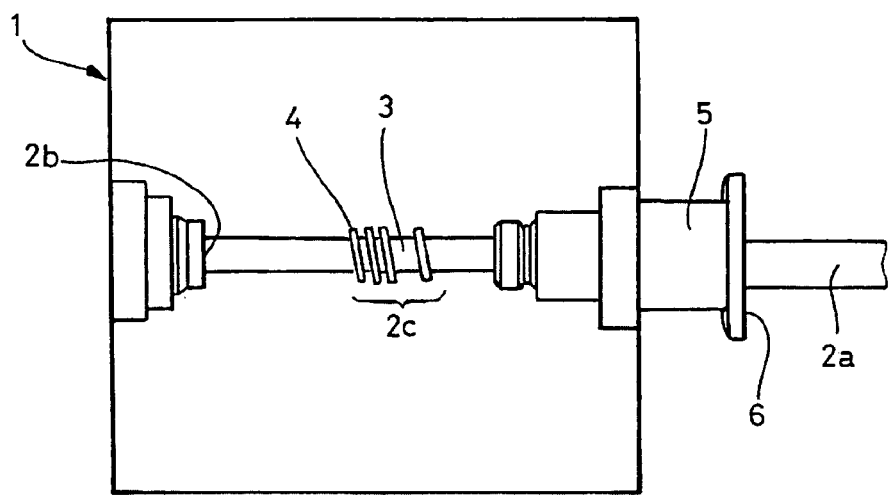
FIG_2
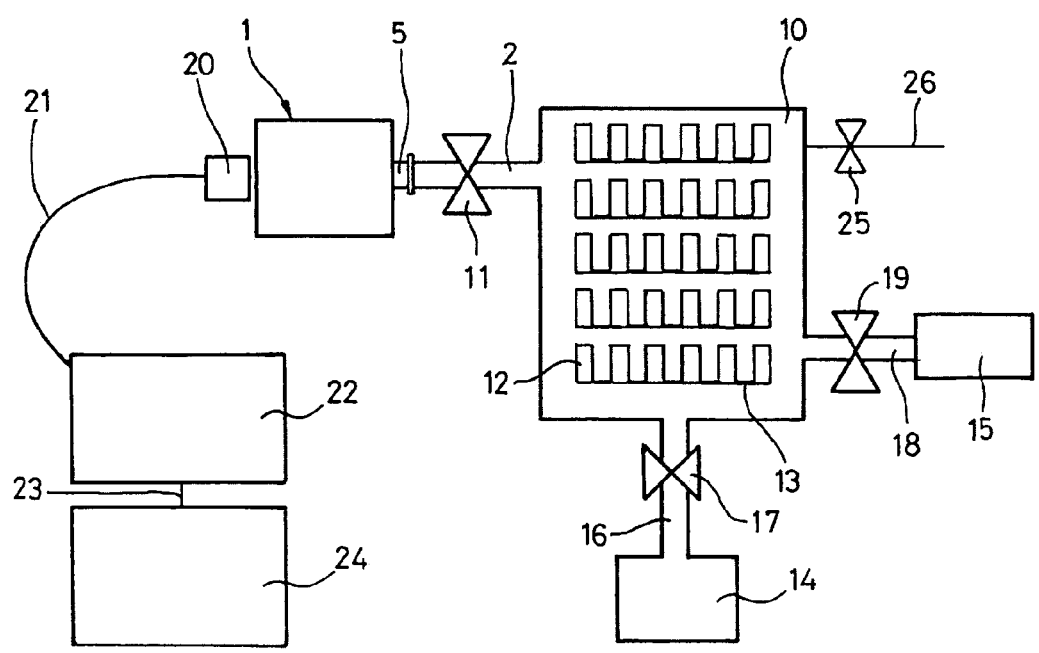

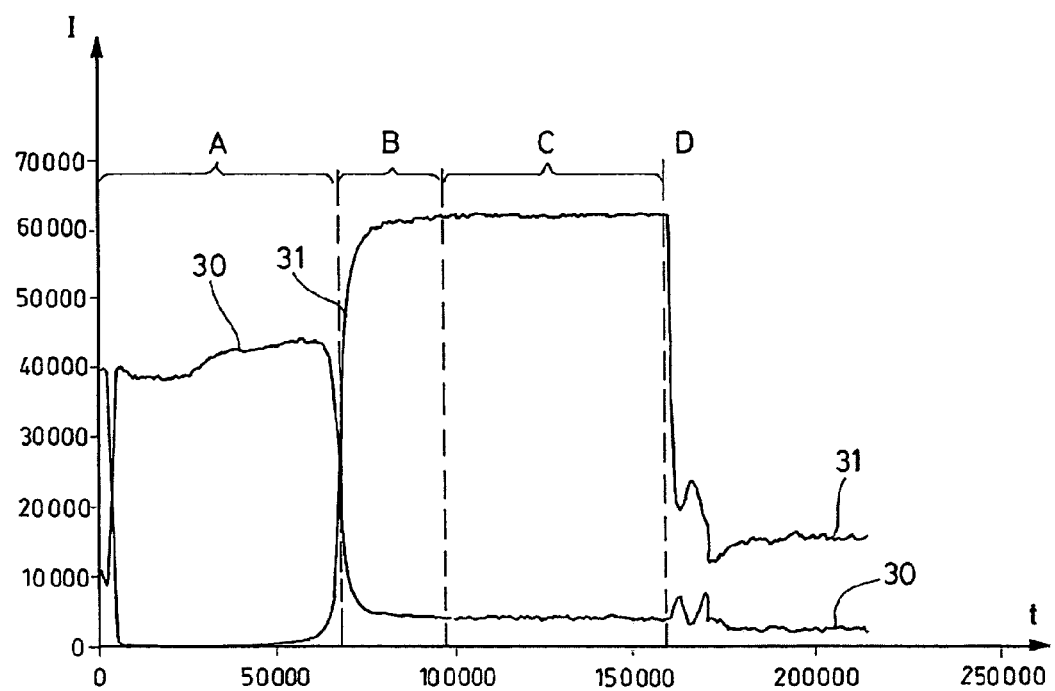

DEVICE AND METHOD FOR CONTROLLING DEHYDRATION DURING FREEZE-DRYING

CROSS-REFERENCE TO RELATED APPLICATIONS

This application is based on French Patent Application No. 04 53 161 filed Dec. 23, 2004, the disclosure of which is hereby incorporated by reference thereto in its entirety, and the priority of which is hereby claimed under 35 U.S.C. § 119.

BACKGROUND OF THE INVENTION

1. Field of the Invention

The present invention relates to monitoring and/or controlling dehydration of products during a vacuum-drying process and more particularly to detecting the end of sublimation of water contained in products subjected to freeze-drying.

2. Description of the Prior Art

Freeze-drying is a low-temperature process that eliminates by sublimation most of the water contained in a product. The industries to which this process is most relevant are the foodstuffs industry, the pharmaceuticals industry (vaccine, serum, medication) and the bio-industries (yeast), the process assuring long-term conservation of an active principle (exhibiting biological and/or medication activity) in a product that will be stored at a temperature close to room temperature.

Monitoring dehydration kinetics during freeze-drying is essential for controlling manufacturing costs and additionally for obtaining a freeze-dried product of good quality. The stability of a product stored under these conditions is extremely sensitive to very small variations in the amount of residual water that it contains. Although it reduces costs, a cycle that is too short yields a product that is too moist. Fast deterioration of the quality of the product is then generally observed. Conversely, an operating cycle that is too long may cause the product to deteriorate through overheating, as well as incurring additional costs with no benefit. Increasing the temperature too early on in the process may lead to fusion or partial fusion of the product, resulting in a defective appearance. This fabrication accident is usually accompanied by significant or even unacceptable degrading of certain of the properties of use required in the end product (purity, suitability for rehydration). Reliable monitoring of the dehydration of such products therefore proves to be essential.

The freeze-drying process comprises two successive operations: freezing and dehydration. The dehydration operation comprises two steps, corresponding to two different physical phenomena: sublimation of ice crystals that are formed during freezing, often referred to as "primary desiccation", and final desorption of water that is not frozen, often referred to as "secondary desiccation". Sublimation is usually achieved by input of heat and reducing the total pressure (vacuum freeze-drying). The problem is to determine the passage from one step to another and the end of the operation as accurately as possible.

The freezing operation is generally conducted at atmospheric pressure. The dehydration operation necessitates reducing the water vapor pressure below the triple point, after which the passage of the water to the vapor state is encouraged by a pressure reduction. Throughout the sublimation step, and for as long as the product contains ice, the temperature of the product will remain identical to the temperature at which it was frozen. When the product contains no more ice, i.e. at the end of primary desiccation, the temperature of the product rises.

The method of monitoring freeze-drying that is most widely used in an industrial environment measures how the temperature of the product evolves during treatment. In particular, this enables the end of primary desiccation to be determined. Temperature probes are placed in the heart of the product before freezing and the evolution of the temperature signal is then recorded during freeze-drying. As long as the probe remains in the frozen heart of the product, the measured temperature evolves very slowly. On the other hand, as soon as the probe is no longer in contact with ice, the measured temperature changes very quickly, which reflects the accumulation of heat in the dry layer. Freeze-drying is stopped (or the set point is changed to begin the secondary desiccation step) when all the temperature probes at different locations in the processing enclosure indicate the same value. Products placed in the same enclosure can exhibit different rates of desiccation, and a difference of several hours in the time to reach the reference temperature may be observed between the various probes. The safety measure that consists in waiting several hours for all the temperature values to be the same before stopping the cycle imposes an additional process cost, which is sometimes high, and reduces efficiency. Moreover, the number of probes used is generally small (of the order of four or five probes for 150 000 products to be freeze-dried), which can lead to a rejection rate of up to 10% for a batch of product.

Other measuring systems have been envisaged for monitoring vacuum freeze-drying kinetics, for example by measuring the electrical resistance or the dielectric constant of the product during treatment. The passage of the front at the electrodes placed in the product varies these magnitudes. Furthermore, the dielectric constant of liquid water being very much higher than that of ice, it is possible to detect melting phenomena.

The major drawback of the above indirect methods is their localized character and lack of sensitivity. The temperature curves are insufficiently accurate and do not enable the exact end of primary desiccation to be determined, for example.

A control method was therefore envisaged that takes account of the whole system. In particular, it was proposed to use a method of monitoring process kinetics based on thermal balances for the heating plates and the ice trap of the freeze-drier. Monitoring the liquid nitrogen consumption of the cold trap enables a thermal balance to be drawn up. In theory this method gives the intensity of the transfer of heat at all times, and consequently the quantity of water vapor produced. However, the quality of the thermal balance is adversely affected by the accuracy of the temperature probes and by thermal losses, which are difficult to quantify.

Measuring the mass of the trays containing the product or of the condenser is one way to monitor water loss kinetics during treatment. The tray-support system or the cold trap fixed to a frame are equipped with strain gages whose deformation can be correlated to the quantity of water extracted from the product and trapped in the form of ice. Unfortunately, this apparently reliable method cannot be easily adapted to most freeze-drying equipment already installed, and its cost remains high. A materials balance for the water vapor given off in the enclosure can equally be obtained by direct measurement using a water vapor pressure sensor. There remains the problem of the accuracy of the measurement at the end of the process for all these methods.

If the condenser is outside the freeze-drying enclosure, it is possible to monitor the evolution of the total pressure in the freeze-drying enclosure after closing a valve connecting the enclosure to the trap (this is called the barometric method). Ignoring air leaks, any fast rise in pressure indicates a high rate of sublimation and reflects the presence of residual ice. The resolution of the method (impact of pressure rise on freeze-drying kinetics) and its accuracy at the end of the cycle (when little water vapor is given off) define its limits.

More recently, a method based on mass spectrometer measurement has been envisaged that analyzes materials balances throughout the freeze-drying enclosure. This method produces the most accurate and the most uniform measurements, leading to true monitoring of dehydration. Unfortunately, in some aseptic process industries, such as the pharmaceuticals industry, sterilization of the measuring equipment is required. The mass spectrometer is not able to withstand sterilization stresses and therefore cannot be sterilized. To solve this problem, a valve fitted with a filter is inserted between the mass spectrometer and the enclosure. This method has certain limitations, however, resulting in particular from clogging of the filters. There is a risk of contamination of the freeze-drying enclosure via the filter. Moreover, the use of a mass spectrometer is costly because it necessitates the use of a secondary pump and the frequent renewal of consumable components like the filament.

Like the method using a mass spectrometer, the other methods proposed also give rise to problems if sterilization proves necessary.

An object of the present invention is therefore to propose a device and a method for controlling dehydration during freeze-drying that does not have the drawbacks of the prior art methods cited above. In particular, the invention proposes a device and a method for determining accurately the end of the primary desiccation step. The invention also proposes a device and a method that are compatible with strict requirements in terms of aseptic conditions, and in particular that avoid recourse to sterilization.

SUMMARY OF THE INVENTION

The present invention is a device for controlling dehydration during freeze-drying in an enclosure connected to a vacuum line, the device including an analyzer for analyzing the gases contained in the enclosure and the gas analyzer comprising:
  a system for ionizing the gases comprising a plasma source in contact with the gases combined with a generator adapted to generate a plasma from the gases, and
  a system for analyzing ionized gases comprising a radiation sensor situated in the vicinity of the area of generation of the plasma connected to apparatus for analyzing evolution of the radiation spectrum emitted by the plasma.

The device of the invention can monitor the evolution of species present in the freeze-drying enclosure during dehydration by analyzing the optical spectrum of light emitted by a plasma consisting of the excited species.

A plasma is a statistical system formed of charged particles and neutral particles that may be created artificially by ionizing a gas. To this end it is necessary to input energy in order to tear electrons off the gas particles and thereby obtain a system of ions, electrons and atoms. This is a globally neutral set of particles that move at random in all directions. Return of the excited molecules to their initial state causes the emission of electromagnetic radiation. Non-thermal plasmas, also known as cold plasmas, appear at reduced pressures: cold plasmas are the most widely used plasmas because of their germicidal properties. Many studies have been carried out on the bactericidal and viricidal properties of the plasma, on reference microorganisms such as *E coli, Bacillus subtilis, Candida albicans, Streptococcus,* etc.

The plasma source is placed in an excitation chamber communicating with the treatment enclosure. The gases in the enclosure are brought in the excitation chamber into contact with the interior of the freeze-drying enclosure containing the products to be dehydrated. The gases are ionized to form a plasma and the light emitted through the walls of the chamber is analyzed.

It is possible to transfer energy to a plasma generating gas by creating an electrical discharge in a confined enclosure, generally containing a partial vacuum:
  either by a system including electrodes (discharge in an electric field of luminescent type at low pressure or of corona type at atmospheric pressure),
  or by a system without electrodes (discharge in a variable radio-frequency or microwave-frequency electromagnetic field).

Thanks to appropriate design of the system and an appropriate choice of the gases and vapors used to generate the plasma, it is possible to achieve a relatively low ambient temperature even in a highly reactive environment. Moreover, active species capable of destroying microorganisms quickly are created only when the system is under power and eliminated immediately the input power is cut off. There is therefore no danger to the environment once the process has terminated.

In one embodiment of the invention, the walls of the chamber are of quartz, optical glass (in particular BK7 glass) or aluminum oxide (in particular sapphire).

The device differs from the prior art devices in that it has the advantage of being completely adapted to the requirements of sterilization. The device necessitates no transfer of matter since it operates on the matter to quantify it without moving it. To this end, only the interior of the excitation chamber of the device comes into contact with the internal environment of the freeze-drying enclosure. This chamber usually takes the form of a tube, generally made of quartz, but may equally be made of optical glass, such as BK7 glass, or of aluminum oxide, such as sapphire, or of any other material enabling electromagnetic waves to pass through it whilst providing access to the light. It may be sterilized without difficulty.

Moreover, the plasma itself is known for its sterilizing properties. Its first strength is ultraviolet emission from the plasma, which is germicidal. Then, the OH and O compounds are essential components of plasma sterilization as used in the medical field. These compounds are encountered in the freeze-drying application because water molecules are "cracked" and so OH and O compounds are generated. Plasma processes are emerging techniques whose potential is particularly promising in a number of sectors, including sterilization, where the efficacy of the plasma technique has been proved and applied in a number of sensitive medical devices.

Moreover, the device guarantees an overall measurement because sublimation of all the products of a batch of products can be viewed, not merely a small sample from the batch.

The plasma source is preferably produced by inductive coupling, in which case the generator is a radio-frequency generator. The plasma source may also be a microwave source using the principle of propagation of a surface wave or of the resonant cavity type, in which case the generator is a microwave generator.

In a first variant, the generator generates the plasma inductively by means of an induction solenoid wound around the outside of the chamber.

In another variant, the generator generates the plasma inductively by means of an excitation antenna disposed inside the chamber. In this case, the antenna is covered beforehand with a sterile insulation. The antenna is advantageously a Penning manometer. The theory of this pressure gage consists in applying a high voltage between two electrodes to form a plasma. The discharge current is proportional to the pressure. This type of gage, widely used to measure pressure, here finds a new application.

The device for analyzing the evolution of the radiation spectrum is preferably an optical emission spectrometer. A combination of optical filters may also be used for selecting the wavelength(s) to be monitored.

The device of the invention can easily be applied to industrial freeze-drying installations. It requires no major modification of the freeze-drying enclosure and, unlike the mass spectrometer, does not necessitate any additional pumping, as the vacuum necessary for the device to function is the same as that necessary for the freeze-drying process.

The invention also consists in a method of controlling dehydration during freeze-drying in an enclosure by means of the above device. The end of the primary desiccation step of the dehydration operation is determined by analyzing the gases in the enclosure by means of a plasma source connected to apparatus for analyzing the evolution of the radiation spectrum emitted by the plasma. That apparatus is preferably an optical emission spectrometer. The plasma source is preferably produced by inductive coupling.

The present invention has the advantage of proposing an accurate, uniform and sterile method of monitoring dehydration during industrial freeze-drying, in particular enabling the end of the primary desiccation step to be determined. This method improves productivity as well as reducing end of cycle rejects.

This method circumvents the variability of the freeze-drying treatment. The various process steps may have different durations, depending on the quantity and the nature of the products to be freeze-dried. This method also provides a significant time-saving: the beginning of the secondary desiccation step, at present determined empirically in industrial processes, may be determined automatically by means of the device of the present invention. This implies savings in terms of the nitrogen used to regulate the pressure. The device naturally takes into account the variations of the parameters of the process that may be operative during dehydration, depending on the quantity the nature of the product to be freeze-dried. This method can also show up the repetitiveness of the process from one batch to another. If the signals are different for the same quantity of product and the same process parameters, this may indicate a problem with the freeze-drier, for example a leak.

Other features and advantages of the present invention will become apparent in the course of the following description of an embodiment of the invention shown in the appended drawings by way of illustrative but nonlimiting example.

BRIEF DESCRIPTION OF THE DRAWINGS

FIG. 1 represents the ionization system of one particular embodiment of the device of the invention.

FIG. 2 shows an installation for freeze-drying products using the invention.

FIG. 3 shows the variation of the luminous intensity I (in arbitrary units) of the hydrogen and nitrogen lines as a function of time t in seconds.

DETAILED DESCRIPTION OF THE PREFERRED EMBODIMENT

FIG. 1 is a diagram of one particular embodiment of the ionization system 1 of a device of the invention. A quartz tube 2 has an open end 2a communicating with the enclosure in which freeze-drying takes place and a closed end 2b in the form of an aspherical lens enabling efficient collection of light. The plasma source 3 is formed in the tube 2 at the level of an induction solenoid 4. The solenoid 4, or excitation antenna, is wound onto the exterior of the tube 2 around the area of formation of the plasma or excitation chamber 2c.

The junction 5 (reference DN16 according to the ISO-KF standard) is of 316 stainless steel. A seal 6 provides the seal between the tube 2 and the junction 5. This seal 6 consists of a fluoroelastomer such as "Viton®" and is therefore able to withstand high temperatures.

The above apparatus is adapted to the sterilization requirements that exist in the field of freeze-drying (steam temperature 150° C. and steam pressure 2 bar): the only portions in contact with the gaseous medium are the tube in which the plasma is formed, the seal and the DN16 junction. The plasma is created by an external antenna, which avoids any contamination or deposition inside the freeze-drying enclosure. The plasma source is relatively compact (for example 86 mm×50 mm×115 mm) and may therefore be placed easily on a freeze-drying enclosure.

FIG. 2 shows one particular embodiment of the device of the invention. The ionization system 1 is associated with a freeze-drying enclosure 10 by its junction 5 and the tube 2 carrying a valve 11. The freeze-drying enclosure 10 that contains products 12 to be dehydrated conventionally comprises three components: a heat source 13, a water vapor recovery trap 14 and a primary vacuum pump 15. The trap 14 is connected to the enclosure 10 by a pipe 16 including a valve 17. The vacuum pump is connected to the enclosure 10 by a pipe 18 including a valve 19. Once freezing, which may be carried out inside or outside the freeze-drying enclosure 10, is complete the vacuum pump 15 is started. The objective of pumping by means of the pump 15 is to reduce the total pressure in the enclosure 10 and then to maintain the pressure at a value compatible with the sublimation conditions throughout dehydration. Sublimation is effected by input of heat to the product from the heat source 13, by conduction or radiation, melting being prevented by maintaining the temperature below the triple point. The trap 4 recovers the water vapor that is formed.

When dehydration begins, the pressure inside the enclosure 10 falls and a plasma is formed inside the tube 2 at the level of the excitation chamber 2c. The light emitted by the plasma is detected at the closed end 2b of the tube 2 by a sensor 20 such as an optical fiber. That light is then conducted to an optical emission spectrometer 22 for analysis therein, for example via an optical fiber 21. The light emitted is characteristic of the compounds present in the plasma and therefore in the freeze-drying enclosure 10. For this application, lines characteristic of hydrogen (for example 656 nm) and nitrogen (for example 337 nm) are monitored during dehydration. Information may be recorded and processed by means of a connection 23 to a computer 24.

During the primary desiccation step, the pressure in the freeze-drying enclosure 10 is stabilized by means of the regulator valve 25 on the nitrogen supply pipe 26. When the pressure falls because of the reduced rate of sublimation, the valve 25 is opened to inject more nitrogen. When the rate of sublimation of the water is high, little nitrogen is injected.

Dehydration is conducted in a vacuum that is generally from 0.005 to 0.5 mbar. In this regard, a plasma source produced by inductive coupling of the inductive coupled plasma (ICP) type, is very suitable because its operating pressure range is from −0.005 mbar to 10 mbar. There is therefore no need for secondary pumping, such as a mass spectrometer could necessitate.

FIG. 3 shows curves 30, 31 obtained by analyzing the optical spectrum. The curves 30, 31 represent the evolution with time of hydrogen lines at a wavelength of 656 nm (curve 30) that represent water vapor and nitrogen lines at a wavelength of 337 nm (curve 31) during the dehydration operation. During the primary desiccation step, a large quantity of water is detected that is caused by sublimation of the ice (part A). This quantity of water vapor evolves little throughout the sublimation phase. When sublimation is completed, the hydrogen signal falls rapidly and the nitrogen signal rises. During this transition, water vapor is replaced by nitrogen injected the freeze-drier (part B). Finally, stabilization of the two curves (part C) marks the end of sublimation and thus the end of primary desiccation. The process curves 30, 31 in FIG. 3 show that the change of set point corresponding to the change to secondary dehydration is triggered at the point D. The prior art measurement of the end of primary desiccation using temperature sensors would have been indicated prior to this, with the step as yet not completely finished.

Of course, the method of detecting the end of the primary desiccation step just described may be applied in the same manner to detecting the end of the secondary desiccation step.

The present invention is not limited to the embodiments explicitly described and includes variants and generalizations thereof that will be evident to the person skilled in the art.

The invention claimed is:

1. A device for controlling dehydration of a product during freeze-drying comprising:
    a freeze-drying enclosure for dehydration of the product, said enclosure being connected to a vacuum line;
    an analyzer for analyzing the gases contained in said enclosure and said gas analyzer comprising:
    a system for ionizing said gases comprising a plasma source in contact with said gases combined with a generator adapted to generate a plasma from said gases, and
    a system for analyzing ionized gases comprising a radiation sensor situated in the vicinity of the area of generation of said plasma connected to an apparatus for analyzing evolution of the radiation spectrum emitted by said plasma.

2. A device according to claim 1, wherein said plasma source is in an excitation chamber communicating with said enclosure.

3. A device according to claim 1, wherein said plasma source is produced by inductive coupling.

4. A device according to claim 3, wherein said generator is a radio-frequency generator.

5. A device according to claim 4, wherein said generator generates said plasma inductively by means of an induction solenoid wound around the outside of said chamber.

6. A device according to claim 4, wherein said generator generates said plasma inductively by means of an excitation antenna inside said chamber.

7. A device according to claim 6, wherein said antenna is a Penning manometer.

8. A device according to claim 1, wherein said analyzer for analyzing the evolution of said radiation spectrum is an optical emission spectrometer.

9. A device according to claim 2, wherein the walls of said chamber are of quartz, optical glass or aluminum oxide.

10. A method of controlling dehydration of a product during freeze-drying in an enclosure connected to a vacuum line by means of a control device comprising:
    dehydrating the product during a vacuum freeze-drying process in a freeze-drying enclosure,
    ionizing the gases contained in said enclosure using a plasma source in contact with said gases combined with a generator adapted to generate a plasma from said gases;
    analyzing the ionized gases using a radiation sensor in the vicinity of the area of generation of said plasma to determine an evolution of the radiation spectrum emitted by said plasma,
    in which method the end of a primary desiccation step of the dehydration operation is detected from the evolution of the radiation spectrum emitted by said plasma.

11. The method according to claim 10, wherein said radiation sensor is an optical emission spectrometer.

12. The method according to claim 10, wherein said plasma source is produced by inductive coupling.

13. The device according to claim 1, wherein the freeze-drying enclosure further comprises:
    a heat source;
    a water vapor recovery trap; and
    a primary vacuum pump.

14. The device according to claim 1, wherein the freeze-drying enclosure contains the product and the product is a food product.

15. The device according to claim 1, wherein the freeze-drying enclosure contains the product and the product is a pharmaceutical product.

16. The device according to claim 1, wherein the device monitors an evolution of species present in the freeze-drying enclosure during dehydration, and
    wherein some of the species are OH and O compounds of water molecules.

17. The method according to claim 10, wherein dehydrating the product during the vacuum freeze-drying process in the freeze-drying enclosure assures long-term conservation of an active principle in the product that exhibits biological or medication activity during storage of the product at a temperature close to room temperature.

18. The method according to claim 10, wherein the primary desiccation is a sublimation of ice crystals that are formed during freezing.

19. The method according to claim 10, wherein the product is a food product.

20. The method according to claim 10, wherein the product is a pharmaceutical product.

* * * * *